(12) United States Patent
Sadowsky et al.

(10) Patent No.: US 9,682,018 B2
(45) Date of Patent: Jun. 20, 2017

(54) DENTURE TOOTH AND MATERIAL

(71) Applicants: Steven Sadowsky, Bainbridge Island, WA (US); Jeffrey W. Stansbury, Centennial, CO (US)

(72) Inventors: Steven Sadowsky, Bainbridge Island, WA (US); Jeffrey W. Stansbury, Centennial, CO (US)

(*) Notice: Subject to any disclaimer, the term of this patent is extended or adjusted under 35 U.S.C. 154(b) by 0 days.

(21) Appl. No.: 14/656,332

(22) Filed: Mar. 12, 2015

(65) Prior Publication Data
US 2015/0257985 A1    Sep. 17, 2015

Related U.S. Application Data

(60) Provisional application No. 61/952,577, filed on Mar. 13, 2014.

(51) Int. Cl.
| A61K 6/083 | (2006.01) |
| C08L 33/10 | (2006.01) |
| B29C 45/00 | (2006.01) |
| B29K 75/00 | (2006.01) |
| B29L 31/00 | (2006.01) |

(52) U.S. Cl.
CPC .......... *A61K 6/083* (2013.01); *B29K 2075/00* (2013.01); *B29L 2031/7536* (2013.01)

(58) Field of Classification Search
None
See application file for complete search history.

(56) References Cited

U.S. PATENT DOCUMENTS

| 5,130,347 A * | 7/1992 | Mitra ................... A61K 6/0017 |
| | | 433/228.1 |
| 5,332,429 A * | 7/1994 | Mitra ................... A61K 6/0088 |
| | | 106/35 |
| 5,525,648 A * | 6/1996 | Aasen .................. A61K 8/8152 |
| | | 523/115 |
| 8,440,098 B2 * | 5/2013 | Neffgen ................ A61K 6/083 |
| | | 252/79.4 |
| 2009/0256108 A1 * | 10/2009 | Neffgen ................ A61K 6/083 |
| | | 252/79.1 |
| 2012/0132104 A1 * | 5/2012 | Ruppert ............... A61K 6/0017 |
| | | 106/15.05 |
| 2015/0257985 A1 * | 9/2015 | Sadowsky .............. A61K 6/083 |
| | | 523/115 |

FOREIGN PATENT DOCUMENTS

GB          2006792 A *   5/1979  ............... C09J 4/00

OTHER PUBLICATIONS

Ben-Et et al., "Application of NMR for the determination of HLB values of nonionic surfactants"; Journal of the American Oil Chemists' Society; 49(8), 499-500 (1972).
Griffin, "Classification of surface-active agents by 'HLB'" J. Soc. Cosmet. Chem.; 1:311-326 (1949).
Guo et al., "Calculation of hydrophile-lipophile balance for polyethoxylated surfactants by group contribution method"; Journal of Colloid and Interface Science; 298(1):441-450 (Jun. 1, 2006).
Tanaka et al., "Polymer properties of resins composed of UDMA and methacrylates with the carboxyl group"; Dental Materials Journal; 20:206-215 (Sep. 2001).
Trapani et al., "Determination of hydrophile-lipophile balance of some polyethoxylated non-ionic surfactants by reversed-phase thin layer chromatography"; International Journal of Pharmaceutics; 116(1):95-99 ( Mar. 14, 1995).
Wolf et al., "In vitro testing of the bond between soft materials used for maxillofacial prostheses and cast titanium"; The Journal of Prosthetic Dentistry; 85(4):401-408 (Apr. 2001).
OECD SIDS, Methacrylic Acid, CAS No. 79-41-4, Dec. 2, 2001, 8 pages total.

* cited by examiner

*Primary Examiner* — Peter A Salamon
(74) *Attorney, Agent, or Firm* — Merchant & Gould, P.C.

(57) ABSTRACT

The present invention relates to a dental polymer composition, in particular to a polymerizable resin composition combining comonomers capable of intermolecular hydrogen bonding with one or more hydrophobic comonomers. Polymers employing the present resin system exhibit high mechanical strength properties that are retained in the presence of water.

29 Claims, 2 Drawing Sheets

DENTURE TOOTH AND MATERIAL

RELATED APPLICATIONS

This application claims the benefit of U.S. Provisional Application No. 61/952,577, filed Mar. 13, 2014, the contents of which are incorporated by reference herein.

FIELD OF THE INVENTION

The present invention relates to a dental polymer composition, in particular to a polymerizable resin composition combining comonomers capable of intermolecular hydrogen bonding with one or more hydrophobic comonomers. Polymers employing the present resin system exhibit high mechanical strength properties that are retained in the presence of water.

BACKGROUND OF THE INVENTION

Dental matrix resins comprising UDMA, known as a high viscosity base monomer, and MAA, a low viscosity acidic monomer are known. Mechanical strength values of polymers prepared using UDMA/MAA resins were reported to be higher than those obtained with UDMA resin or with a conventional Bis-GMA/TEGDMA/UDMA resin. Tanaka et al., Polymer properties of resins composed of UDMA and methacrylates with the carboxyl group. Dental Materials Journal 2001; 20:206-215.

Unfortunately, while polymers prepared from UDMA/MAA have high strength, they are also relatively hydrophilic and the properties of the materials decline when they are used in dental applications. A denture tooth material that has greater strength and toughness than dental composite restoratives while also offering exceptional clinical performance and durability in the presence of water is desirable.

SUMMARY OF THE INVENTION

The present disclosure relates to an improved dental tooth, and materials and methods for preparation thereof. A polymerizable composition is disclosed combining a urethane monomer, an acidic monomer and one or more hydrophobic comonomers. In some embodiments, the disclosure provides a polymerizable resin composition comprises a urethane monomer, an acidic monomer, one or more hydrophobic monomers and further comprises a surfactant and/or a prepolymer.

In some embodiments, the urethane monomer is selected from 1,6-bis(methacryloxy-2-ethoxycarbonylamino)-2,2,4 (2,4,4)-trimethylhexane (UDMA) or bis(2-(methacryloyloxy)ethyl) 5,7,7,24,24,26-hexamethyl-10,21-dioxo-11,14, 17,20-tetraoxa-2,9,22,29-tetraazatriacontanedioate.

In some embodiments, the acidic monomer is selected from the group consisting of methacrylic acid (MAA), bis (2-methacryloxyethyl) phthalate, pyromellitic glycerol dimethacrylate, methacroyloxyethyl maleate, hydroxyethyl methacrylate/succinate adduct, 1,3-glycerol dimethacrylate/maleate adduct and 1,3-glycerol dimethacrylate/succinate adduct.

In some embodiments, the hydrophobic monomer is selected from the group consisting of isostearyl methacrylate (ISMA), ethoxylated bisphenol A dimethacrylate (BisEMA; EBDMA), stearyl methacrylate, lauryl methacrylate, isodecyl methacrylate, 2-ethylhexyl methacrylate and cyclohexyl methacrylate.

In some embodiments, the surfactant is selected from sodium dodecyl sulfate (SDS), ammonium lauryl sulfate, Cetyl trimethylammonium bromide (CTAB), Cetylpyridinium chloride (CPC), Polyethoxylated tallow amine (POEA); Dodecyl betaine, Dodecyl dimethylamine oxide, sodium lauryl sulfate and polyether modified polydimethylsiloxane (BYK®-307).

In some embodiments, the resin composition further comprises a prepolymer is formed from a resin composition comprising methyl methacrylate (MMA) or isobornyl methacrylate (IBMA).

The disclosure further provides a method of preparing a shaped dental prosthetic device for use in a human mouth, the method comprising dispensing a resin composition comprising a urethane monomer and one or more hydrophobic monomers; shaping the mixture into the form of the shaped dental prosthetic device; and photopolymerizing the shaped mixture.

The disclosure further provides a dental prosthetic device comprising a polymer created from the polymerization of the resin comprising a urethane monomer, one or more hydrophobic monomers and an acidic monomer in admixture with one or more fillers.

The disclosure further provides a dental restorative material comprising particles of filler and the resin composition comprising a urethane monomer, one or more hydrophobic monomers and an acidic monomer. In some embodiments, the filler is present at 40 wt % to 90 wt % of the total material weight. In some embodiments, the filler is present at 70 wt % to 85 wt % of the total material weight. In some embodiments, the filler is present at 75 wt % to 80 wt % of the total material weight.

In some embodiments, the disclosure provides a dispensing device comprising an unpolymerized quantity of a polymerizable dental restorative material comprising a urethane monomer, one or more hydrophobic monomers, an acidic monomer, and a filler comprising 40 wt % to 90 wt % of the total material weight.

DETAILED DESCRIPTION OF THE INVENTION

Figure 1:
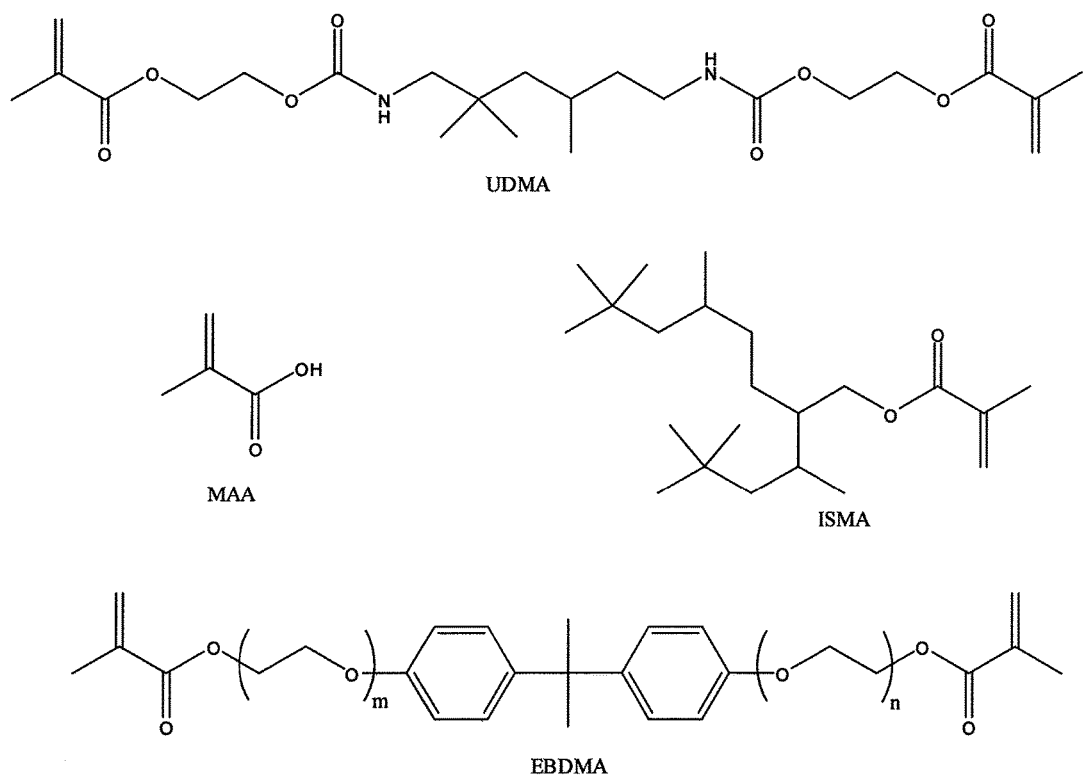
FIG. 1 shows monomer components employed in a polymerizable resin composition of the disclosure.

The disclosure provides a new denture tooth material that has greater strength and toughness than dental composite restoratives while also offering exceptional clinical performance and durability. The design of strong intermolecular hydrogen bonding combined with the use of hydrophobic comonomers gives a unique resin system with uniquely high mechanical strength properties that are retained in the presence of water.

DEFINITIONS

A "polymer" is a substance composed of macromolecules. A polymer macromolecule is a molecule of high relative molecular mass, the structure of which comprises the multiple repetition of units derived from molecules of low relative molecular mass.

A "branched polymer" is a polymer that includes side chains of repeat units connecting onto the main chain of repeat units (different from side chains already present in the monomers). A branched polymer refers to a non-linear polymer structure, but typically, not a network structure. Therefore, a trace forward from the branch point would not bridge back to the original main chain; i.e. minimal to no backbone crosslinking is present. A branched polymer would generally be soluble in an appropriate solvent.

A "crosslinked polymer" is a polymer that includes interconnections between chains, either formed during polymerization (by choice of monomer) or after polymerization (by addition of a specific reagent). In a crosslinked polymer network, with the crosslinks serving as branch points, it is possible to trace a continuous loop back to the backbone. The crosslinked network would be insoluble in all solvents.

A "network polymer" is a crosslinked polymer that includes two or more connections, on average, between chains such that the entire sample is, or could be, a single molecule. Limited crosslink connections per chain would be considered lightly crosslinked while numerous crosslinks would be considered highly (or heavily) crosslinked.

A "copolymer" is a material created by polymerizing a mixture of two, or more, starting compounds. The resultant polymer molecules contain the monomers in a proportion which is related both to the mole fraction of the monomers in the starting mixture and to the reaction mechanism.

A "chain transfer agent" is an intentionally added compound that terminates the growth of one polymer chain and then reinitiates polymerization to create a new chain. A chain transfer agent is used as a way to limit chain length.

"Gelation time" is the time to reach the gel point (the point at which a continuous crosslinked network initially develops) during a polymerization.

A "filler" is a solid extender which may be added to a polymer to modify mechanical, optical, electrical, thermal, flammable properties, or simply to act as an extender. The filler can be reactive or inert in the polymerization.

An "extender" is a substance added to a polymer to increase its volume without substantially altering the desirable properties of the polymer.

The term "urethane monomer" refers to a monomer comprising two or more acrylate/methacylate groups and two or more urethane groups. The term encompasses various urethane dimethacrylates including, but not limited to 1,6-bis(methacryloxy-2-ethoxycarbonylamino)-2,2,4(2,4,4)-trimethylhexane (urethane dimethacrylate, UDMA, RN:72869-86-4) (RN: 41137-60-4) and bis(2-(methacryloyloxy)ethyl) 5,7,7,24,24,26-hexamethyl-10,21-dioxo-11,14,17,20-tetraoxa-2,9,22,29-tetraazatriacontanedioate (RN: 94333-55-8).

The term "acidic monomer" refers to a monomer having at least one acrylate/methacylate group and at least one carboxylic acid group. The term encompasses, but is not limited to methacrylic acid (MAA).

The term "hydrophobic monomer" refers to a monomer having one or more acrylate/methacrylate groups and no urethane, carboxylic acid, or hydroxyl functional groups. Hydrophobicity of monomers can also be assessed and compared using the n-octanol-water distribution coefficient (log $P_{o/w}$). For example, methyl methacrylate has a log octanol/water partition coefficient (log Kow) of 0.79. U.S. Environmental Protection Agency. *Health and Environmental Effects Profile for Methyl Methacrylate*. EPA/600/x-85/364. Environmental Criteria and Assessment Office, Office of Health and Environmental Assessment, Office of Research and Development, Cincinnati, Ohio. 1985.

The term "alkyl", "aliphatic" or "aliphatic group" as used herein means a straight-chain or branched $C_{1-20}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable alkyl groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkoxy," "hydroxyalkyl," "alkoxyalkyl" and "alkoxycarbonyl," used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

Synthetic polymers have a distribution of molecular weights (MW, grams/mole). Polydispersity describes a polymer consisting of molecules with a variety of chain lengths and molecular weights. The width of a polymer's molecular weight distribution is estimated by calculating its polydispersity, Mw/Mn. The closer this approaches a value of 1, the narrower is the polymer's molecular weight distribution.

Figure 2:
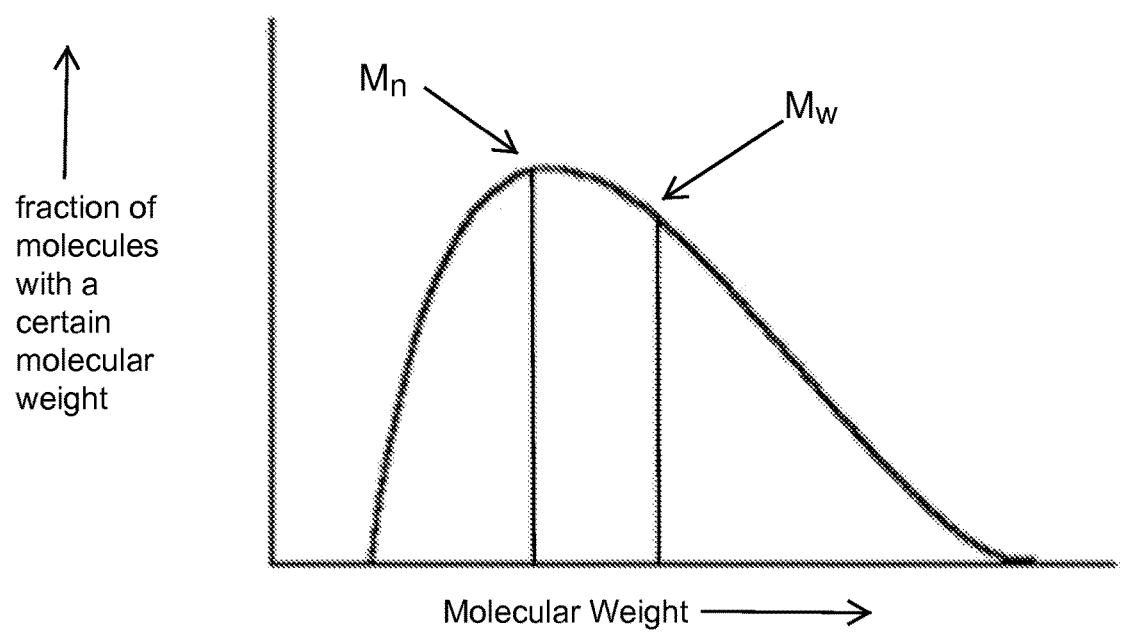
FIG. 2 shows a graph of molecular weight vs. fraction of molecules with a certain molecular weight for a polydisperse polymer sample, illustrating weight-average molecular weight (Mw), as the average molecular weight of a polydisperse polymer sample, averaged to give higher statistical weight to larger molecules; and number-average molecular weight (Mn), as the average molecular weight of a polydisperse polymer sample, averaged to give equal statistical weight to each molecule.

The weight-average molecular weight (Mw), as illustrated in FIG. 2, is the average molecular weight of a polydisperse polymer sample, averaged to give higher statistical weight to larger molecules; calculated as Mw=SUM ($Mi^2$ Ni)/SUM (Mi Ni), where Ni is the number of molecules of molecular weight Mi. One technique used to measure molecular weights of polymers is light scattering. A light shining through a very dilute solution of a polymer is scattered by the polymer molecules. The scattering intensity at any given angle is a function of the second power of the molecular weight. Consequently, because of this "square" function, large molecules will contribute much more to the molecular weight that we calculate than small molecules.

The number-average molecular weight (Mn), as illustrated in FIG. 2, is the average molecular weight of a polydisperse polymer sample, averaged to give equal statistical weight to each molecule; calculated as Mn=SUM (Mi Ni)/SUM (Ni), where Ni is the number of molecules of molecular weight Mi.

Monomers

The problem to be solved was to develop a new denture tooth material that has greater strength and toughness than dental composite restoratives while also offering exceptional clinical performance and durability. The design of strong intermolecular hydrogen bonding combined with the use of hydrophobic comonomers gives a unique resin system with uniquely high mechanical strength properties that are retained in the presence of water.

In some embodiments, the disclosure provides a polymerizable resin composition comprising a urethane monomer comprising two or more methacylate groups and two or more urethane groups capable of intermolecular hydrogen bonding, and one or more hydrophobic monomers.

In some embodiments, the disclosure provides a polymerizable resin composition comprising a urethane monomer, an acidic monomer and one or more hydrophobic monomers.

In some embodiments, the disclosure provides a composition comprising a urethane monomer, an acidic monomer, one or more hydrophobic monomers and one or more surfactants.

Urethane Monomers

The term urethane monomer is a monomer having two or more acrylate/methacrylate groups and one or more urethane groups. In embodiments, various urethane dimethacrylates are employed including, but not limited to 1,6-bis(methacryloxy-2-ethoxycarbonylamino)-2,2,4(2,4,4)-trimethylhexane (urethane dimethacrylate, UDMA, RN:72869-86-4) (RN: 41137-60-4) and bis(2-(methacryloyloxy)ethyl) 5,7,7,24,24, 26-hexamethyl-10,21-dioxo-11,14,17,20-tetraoxa-2,9,22, 29-tetraazatriacontanedioate (RN: 94333-55-8). The urethane group has the ability to hydrogen bond by acting as a hydrogen bond donor or hydrogen bond acceptor (e.g., urethane N—H can act as a hydrogen bond donor; urethane C=O can act as a hydrogen bond acceptor). In some preferred embodiments, the urethane monomer is urethane dimethacrylate (UDMA). In some embodiments, the UDMA monomer is specifically 1,6-bis(methacryloxy-2-ethoxycarbonylamino)-2,2,4(2,4,4)-trimethylhexane. There are several alternative monomers that could be substituted for UDMA, including other urethane-containing multi-(meth) acrylates, such as oligomeric urethane (meth)acrylates. A consideration with any alternate urethane (meth)acrylates is that the methacrylate structure is preferred to provide greater mechanical strength polymer networks, and also that the urethane functional groups are readily accessible such that strong hydrogen bonding interactions with the carboxylic acid groups in the copolymer are not hindered. The chemical structure of UDMA is illustrated in FIG. 1.

Acidic Monomers

In some embodiments, acidic monomer is selected from methacrylic acid (MAA), bis (2-methacryloxyethyl) phthalate, pyromellitic glycerol dimethacrylate, methacroyloxyethyl maleate, hydroxyethyl methacrylate/succinate adduct, 1,3-glycerol dimethacrylate/maleate adduct or 1,3-glycerol dimethacrylate/succinate adduct. Other acidic monomers can be used in place of MAA, but the typical aromatic mono- or di-acid functional monomers, such as methacryloxyethyl phthalate or pyromellitic glycerol dimethacrylate, do not provide the high mechanical strength found with UDMA/MAA copolymers probably due to the steric restriction associated with the aromatic ring. Otherwise, acidic monomers such as methacroyloxyethyl maleate, hydroxyethyl methacrylate/succinate adduct, 1,3-glycerol dimethacrylate/maleate adduct or 1,3-glycerol dimethacrylate/succinate adduct can be employed. However, increased spacing between the acidic and polymerizable functional groups might affect the high strength potential of the copolymers with UDMA or other urethane-based monomers. In some embodiments, the polymerizable resin composition comprises an acidic monomer selected from methacrylic acid and acrylic acid or other —COOH containing monomers. In some embodiments, the resin compositions comprise MAA monomer. In some embodiments, the compositions do not comprise MAA.

The urethane group of the urethane monomer and the carboxyl group of the acidic monomer are capable of intermolecular hydrogen bonding. In some embodiments, the urethane monomer is urethane dimethacrylate (UDMA) and the acidic monomer is methacrylic acid (MAA). The optimal properties are obtained when there is a stoichiometric balance between hydrogen bond accepting groups on a first comonomer and hydrogen bond donor groups on a second comonomer. UDMA contains two urethane groups capable of acting as hydrogen bond donors or acceptors. The carboxylic acid group of MAA is capable of acting as a hydrogen bond acceptor (e.g., C=O), or donor ($CO_2H$) depending on pH of the composition. UDMA has two urethane groups per molecule, while MAA has one carboxylic acid group per molecule. UDMA has two urethane groups and is capable of forming at least two hydrogen bonds. MAA has a single carboxylic acid group and is capable of forming at least one hydrogen bond. Therefore, for example, a 1:2 molar ratio of UDMA/MAA was used in several embodiments. Polymerization of these materials is often assisted by pressure and/or heat to maximize their conversion and properties.

It should be noted that MAA is not generally considered a suitable comonomer for dentistry in general because of the at least mildly unpleasant odor of MAA. As most dental materials are first and foremost used in direct fill situations (meaning the material is placed in the patient's mouth in the monomeric state and cured in place), this explains why MAA has been ignored as a dental material.

However, the present research indicates that MAA can appropriately be applied in indirect dental materials which are lab cured materials that are then used as cemented inlays/onlays and crowns as well as denture teeth. In these applications, the drawback of odor is no longer important.

Another reason why UDMA/MAA have not generally been used in dentistry is that while polymers from UDMA/MAA have high strength, they also are relatively hydrophilic and the properties of the material decline when used in dental applications.

However, the present research has shown that, while the initial properties decline somewhat, the extent of the decline is not as much as one might think and the material's properties are still quite good. In addition, the disclosure provides compositions which incorporate additional non-hydrogen bonding hydrophobic monomers that are designed to not interfere with the desired reinforcing interactions between UDMA and MAA while also providing more hydrophobic polymers with the potential to achieve very high conversion, which is another important point to assure long-term stability of the polymer properties.

To achieve this, we have incorporated ethoxylated bisphenol A dimethacrylate (EBDMA) and isostearyl methacrylate (ISMA) along with the UDMA and MAA. We also evaluated the material composition with MAA removed. The ISMA is commercially available but, to the best of the inventor's knowledge, has not previously been used in dental materials applications. The ISMA improves the conversion of the final cured polymer, thus improving the hardness (as measured by the Vicker's hardness) and stiffness (as measured by the Young's modulus). It also assists in making the cured polymer hydrophobic and thus counters the hydrophilic nature of MAA.

As used herein, the urethane monomers and the acidic monomers are considered to be hydrogen-bond forming monomers. In some embodiments, the disclosure provides polymerizable resin compositions comprising hydrogen-bond forming monomers (urethane monomers and acidic monomers) and hydrophobic monomers, wherein the weight ratio of hydrogen-bond forming monomers to hydrophobic monomers is from 99:1 to 50:50; 90:10 to 60:40; or 85:15 to 75:25, or about 80:20.

Hydrophobic Monomers

The polymerizable resin compositions comprise one or more hydrophobic monomers comprising one or more acrylate or methacrylate groups. In some embodiments the hydrophobic monomer is selected from one or more of Isostearyl methacrylate (ISMA), Ethoxylated bisphenol A dimethacrylate (BisEMA; EBDMA), stearyl methacrylate, lauryl methacrylate, isodecyl methacrylate, 2-ethylhexyl methacrylate and cyclohexyl methacrylate. In some embodiments, the hydrophobic monomer is a hydrophobic cross-linker such as Ethoxylated bisphenol A dimethacrylate (BisEMA; EBDMA). In some embodiments, the hydrophobic monomer is a combination of Ethoxylated bisphenol A dimethacrylate (BisEMA; EBDMA) and Isostearyl methacrylate (ISMA). In some embodiments, the hydrophobic monomer is Isostearyl methacrylate (ISMA). In some embodiments, a cross linking monomer such as BisEMA is employed. The ISMA provides extreme hydrophobic character that also promotes both high conversion and stain resistance. The highly branched ISMA structure also contributes sub-nanometer sites with greater localized mobility that serve to absorb mechanical energy and thereby enhance toughness in the copolymer. In some aspects, the use of the branched ISMA structure rather than a linear stearyl methacrylate is preferred since the latter is more prone to the formation of phase-separated semi-crystalline domains that could negatively affect the translucency of the final polymer.

There are several roles that each of these monomers has within the uncured liquid resin and in the final, fully cured polymer. Of primary importance is the combination of UDMA and MAA in a stoichiometric (or near) balance of urethane and carboxylic acid functional groups (one mole of the difunctional UDMA with two moles of the monofunctional MAA) as previously disclosed in the publication of Tanaka et al., 2001, Dental Materials J, 20(3): 206-215. If the functional groups are imbalanced, the excess monomer should be IUDMA since the mechanical strength of the UDMA/MAA copolymers drops quickly when MAA is the excess reactant. It is the strong and extended intermolecular hydrogen bonding interactions between UDMA and MAA that are mainly responsible for the favorable combination of very high mechanical strength and toughness. Because of the strength of these hydrogen bonding interactions, the polymeric mechanical properties are maintained even in a wet, challenging environment. This advantageous combination of strength and toughness is critical for avoiding wear and chipping of the denture tooth edges. The BisEMA serves as hydrophobic crosslinker that raises the overall crosslink density while also contributing a relatively high refractive index that enhances the translucent character of the filled polymer. By increasing the ratio of BisEMA to ISMA used in the resin phase, the refractive index of the material can be increased. Pigments and opacifiers can be added as needed to achieve specific esthetic and optical properties. It would be expected that although BisGMA typically provides greater strength copolymers compared with the use of BisEMA, in this case, the hydroxyl groups in the BisGMA structure would interfere with the preferred hydrogen bonding between UDMA and MAA. Additionally, BisGMA would reduce the limiting conversion and therefore, its use is not recommended here although it would provide a route to increased resin viscosity if that were an important formulation issue.

Dentures are prosthetic devices constructed to replace missing teeth, and which are supported by surrounding soft and hard tissues of the oral cavity. Conventional dentures are removable, however there are many different denture designs, some which rely on bonding or clipping onto teeth or dental implants. There are two main categories of dentures, depending on whether they are used to replace missing teeth on the mandibular arch or the maxillary arch. There are many informal names for dentures such as dental plate, false teeth and falsies.

An important aspect of denture construction is the manufacture of the denture teeth. Denture teeth refers to the teeth of the denture which may be made of a different material than the remainder of the denture. Such denture teeth should be mechanically strong in order to resist breakage during use. The measurement of mechanical strength is well known in the art and any suitable method may be used to characterize a denture tooth material.

In addition to bulk mechanical strength, a dental material's surface hardness is also a factor that will affect relevant properties such as its ability to be polished to a smooth surface and then the related ability to retain its surface finish based on scratch resistance. The surface hardness is evaluated by indentation of the material with a well-defined indenter geometry and force. A Vickers hardness test brings a square pyramidal shaped indenter into contact with the material surface. Under constant load, the indenter sinks into the surface through a yielding deformation of the material until the contact area increases to the point that the actual stress is equivalent to the yield strength of the material. At this equilibrium point, continued penetration stops and after a suitable dwell time, the indenter is removed. The average length of the diagonals created by the indentation is measured and the Vickers hardness ($H_V$) is calculated by:

$$H_V = (2F/d^2) \cdot \sin(136°/2) = 1.854 F/d^2 \qquad \text{(Equation 1)}$$

where F is the applied force (in kg) and d is the length of the diagonal (in mm).

Another feature of a good denture tooth is its stiffness. The modulus of a material is a measure of its stiffness or resistance to deformation. It is obtained as the slope of the linear portion of the stress-strain curve. Testing involves the application of a limited strain which, up to the proportional limit of the material, induces a purely elastic stress that is completely recoverable when the strain is removed. The material can be tested in either compressive, tensile or flexural modes; however, somewhat different modulus values are obtained depending on the material and the test mode. The modulus also can be obtained from a test of the ultimate strength of a material if only the initial linear region of the stress-strain curve is considered. With stress having units of Pa (based on the force (in N) divided by cross-sectional area (in $m^2$)) and strain having dimensionless units (since a deformation can be measured as a percentage), the unit for modulus is Pa.

In some embodiments, the disclosure provides a polymerizable resin composition suitable for preparation of denture teeth. In some embodiments, the disclosure provides a resin composition comprising at least one urethane monomer capable of forming intramolecular hydrogen bonds, and one or more hydrophobic monomers.

The disclosure also relates to new and improved denture teeth made using a process and material prepared by polymerization of a composition comprising a resin composition comprising a combination of a mixture of one or more urethane monomers and one or more acidic monomers, and one or more hydrophobic monomers.

In some embodiments, the denture tooth is made with UDMA/EBDMA/ISMA mixture with, or without, MAA. In some embodiments, when MAA is used, UDMA/MAA molar ratio is at 1:2+/−20% in approximately stoichiometric amounts with UDMA.

As disclosed herein, research indicates a denture tooth can be created comprising a polymerized mixture of urethane dimethacrylate (UDMA), ethoxylated bisphenol A dimethacrylate (EBDMA) and isostearyl methacrylate (ISMA) and at least 75% by weight of a filler, wherein the denture has a Vickers hardness of at least 75 kgf/(square mm). Further, a denture tooth made of this material will have a greater than 92% conversion and preferably a conversion greater than 96%. It may have a Young's modulus of 4 GPa or greater without the use of a filler and so exhibit excellent stiffness properties. If fillers are used, a Young's modulus of greater than 10 GPa and even 15 GPa should be obtainable. This is anticipated to require very high loading of filler, on the order of 75% to as much as 90% or more. However, the material is suitable for such high loadings. As discussed above, a Vickers Hardness of greater than 60 and even 80 kgf/(square mm) has been demonstrated but greater than 100 is anticipated.

Denture Tooth Fabrication

Another aspect of the present application is the fabrication of the denture tooth. A notable component of the fabrication of the denture tooth is a unique step that includes the preparation of the internal surface of the denture tooth with a microadhesion technique (Rocatec-system 3M, Espe, St. Paul, Minn.) and, in an embodiment, with diatorics (macroadhesive undecuts), along with a bonding agent such as Dentacolor connector (Heraeus Kulzer, Wehrheim, Germany). This bonding agent is a methacrylate. Information on this bonding agent and others (for a different application) is discussed in an article in the JPD 2001; 85:401-8, by Burkhard Wolf. The step may be done at the mold stage after the denture tooth is fabricated or at the stage of denture processing when the flasking procedure allows for isolation of the internal aspects of the teeth. The purpose of these additional steps is to allow bonding of the composite resin denture tooth to the denture matrix with minimal microleakage.

In some embodiments, the denture tooth is fabricated by use of a polymerizable resin composition comprising a urethane monomer, an acidic monomer and one or more hydrophobic monomers.

In some embodiments, the denture tooth is fabricated by use of a polymerizable resin comprising a urethane monomer, one or more hydrophobic monomers and a surfactant.

Prepolymers

In some embodiments, the denture tooth is fabricated by use of a polymerizable resin comprising a urethane monomer, one or more hydrophobic monomers and a prepolymer.

In some embodiments, the disclosure provides a composition comprising a urethane monomer, an acidic monomer, two or more hydrophobic monomers, a prepolymer, an initiator, and one or more fillers.

In some embodiments, the disclosure provides a prepolymer prepared from a polymerizable resin composition comprising a methacrylate/acrylate monomer such as MMA and a hydrophilic monomer comprising at least one acrylate or methacrylate and at least one hydroxyl group is employed. In some embodiments, a hydroxyl group containing monomer is employed in preparation of an optional prepolymer. In some embodiments, the hydroxyl group containing monomer is selected from hydroxy alkyl acrylates such as hydroxy ethylacrylate (HEA); hydroxy alkyl (meth)acrylates such as hydroxyethyl(meth)acrylate (HEMA), hydroxypropyl(meth)acrylate and hydroxybutyl (meth)acrylate. In some embodiments, the hydroxyl group containing monomer is not 2,2'-bis [4-(3-methacryloxy-2-hydroxy propoxy)-phenyl]propane (bis-GMA).

In some embodiments, a isocyanato group containing monomer is employed in preparation of a prepolymer. In some embodiments, the isocyanato group containing monomer is selected from and isocyanatomethyl(meth)acrylate and isocyanatoethyl (meth)acrylate (IEM).

Fillers

The ability to widely alter the filler loading without sacrifice to the strength and toughness makes the present invention well suited for use as a denture tooth material. The overall filler content also allows the modulus and surface hardness of the polymerized composite material to be altered with higher filler contents (especially when the OX50 nanofiller is included) leading to reduced wear rates. The filler content also aids in control of the coefficient of thermal expansion and is directly related to the x-ray opacity of the composite material.

There is no restriction in the type of filler that can be utilized in the filled compositions of the invention. In some embodiments, the filler material is selected from one or more of quartz, strontium, zirconium, and ytterbium-based particulate fillers. In some embodiments, the filler is selected from Ba glass, fumed silica, and ytterbium fluoride. In some embodiments, the filler phase is prepared from a bimodal mixture of barium glass with (Ba glass) and fumed silica (OX50). In some embodiments, the filler is ytterbium fluoride. In some embodiments, the filler employed in the filled polymer is Ba glass/OX50. In some embodiments, the filler is Ba glass/OX50/Yb. In some embodiments a mass ratio of 9:1 Ba glass/OX50 is employed. In some embodiments, the filler phase contains a silane methacrylate surface treatment (gamma-methacryloxypropyltrimethoxysilane. In some embodiments, the filler phase is prepared from a bimodal mixture of barium glass with methacrylate silane surface treatment (Ba glass) and fumed silica with methacrylate silane surface treatment (OX50). In some embodiments, the filler is ytterbium (Yb) glass with methacrylate silane surface treatment. In some embodiments, the surfaces of the filler are coated with a surfactant. In some embodiments, an OX50 nanofiller is employed. In some embodiments, filler is added between about 40 and 85 wt % with respect to the overall composite composition. In some embodiments one or more fillers is present at 75 wt % of higher compared to the weight of the filled composition. In some embodiments, one or more fillers is used at 85 wt % or higher compared to the weight of the filled composition.

The filler provides a dough-like consistency for the composite material in the monomeric state. The paste consistency can be raised or reduced depending on the choice of filler, ratio of the fillers and the filler loading level used. The optical properties of the paste and the final polymerized composite material depend on the degree of mismatch between the refractive indices of the fillers and the resin phase as well as the degree of conversion achieved during the polymerization process. A high degree of conversion (preferably 95% or higher) is desirable to maximize the mechanical properties of the polymeric material while minimizing or avoiding any leachable free monomer.

Initiators

The polymerization of the monomers may be initiated by any suitable method of generating free-radicals such as by thermally induced decomposition of a thermal initiator such as an azo compound, peroxide or peroxyester. Alternatively, redox initiation or photo-initiation can be used to generate the reactive free radicals. Therefore the polymerization mixture also preferably contains a polymerization initiator which may be any of those known and conventionally used in free-radical polymerization reactions, e.g. azo initiators such as 2,2'azobis(isobutyronitrile) (AIBN), azobis(2-methylbutyronitrile), azobis(2,4-dimethylvaleronitrile), 4,4-azobis(4-cyanovaleric acid), 1,1'-azobis(cyclohexanecarbonitrile); peroxides such as benzoyl peroxide, dilauroyl peroxide, tert-butyl peroxyneodecanoate, dibenzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-Butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butylperoxy isopropyl carbonate, cyclohexanone peroxide, dicumyl peroxide, lauroyl peroxide, 2,4-pentanedione peroxide, peracetic acid, cumyl peroxide, tert-butyl peroxy-2-ethyl hexanoate, tert-butyl peroxy diethyl acetate, tert-amyl peroxybenzoate, and tert-butyl peroxy benzoate. In some embodiments, the thermal initiator is benzoyl peroxide (BPO). The BPO has been effectively used at concentrations between 0.85 and 2 wt % relative to the resin phase. The preferred concentration is 1.35-1.85 wt %. In some embodiments, the thermal initiator is AIBN.

In another aspect, the initiator is a redox (reduction-oxidation) pair of initiators. Redox initiator systems use both a primary initiator and a chemical reducing agent. Several types of redox initiator pairs are known such as persulfite-bisulfite, persulfate-thiosulfate, persulfate-formaldehyde sulfoxylate, peroxide-formaldehyde sulfoxylate, peroxide-metallic ion (reduced), persulfate-metallic ion (reduced), benzoyl peroxide-benzene phosphinic acid, and benzoyl peroxide-amine wherein the amine acts as the reducing agent. The redox pair may be selected from any known redox pair such as a combination of benzoyl peroxide and dimethyl-p-toluidine, AMPS (ammonium persulfate) and TEMED (tetramethyl ethylene diamine), sulfur dioxide and tert-butyl hydroperoxide, potassium persulfate and acetone sodium bisulfite. In a specific aspect, the redox initiator pair is 1 wt % benzoyl peroxide with 1.5 wt % dimethyl-p-toluidine amine coinitiator.

In a one aspect, the initiator is a photoinitiator. The photoinitiator can be selected from one or more known photoinitiators. For example, the initiator can be selected from one or more of an alpha-hydroxyketone, an acyl phosphine oxide, a benzoyl peroxide with or without an amine co-initiator. Any known photoinitiator, or combination of one or more photoinitiators can be employed. For example, the photoinitiator can be selected from one or more acyl phosphine oxides such as BAPO (bis-acylphosphine oxide), phenyl-bis(2,4,6-trimethylbenzoyl)phosphine oxide, TPO (2,4,6-trimethylbenzolyldiphenylphosphine oxide), bis-trimethoxybenzoyl-phenylphosphine oxide, TPO-L (2,4,6-trimethylbenzoylphenyl phosphinate), or MAPO (tris[1-(2-methyl)aziridinyl]phosphine oxide. Other photoinitiators may be employed alone or in combination including, but not limited to, DMPA (2,2-dimethoxy-2-phenylacetophenone), BDK (benzil dimethylketal), CPK (cyclohexylphenylketone), HDMAP (2-hydroxy-2-methyl-1-phenyl propanone), ITX (isopropylthioxanthrone), HMPP (hydroxyethyl-substituted alpha-hydroxyketone), MMMP (2-methyl-4'-(methylthio)-2-morpholinopropiophenone), BDMB (2-benzil-2-dimethylamino-1-(4-morpholinophenyl)-butanone-1), BP (Benzophenone), TPMK (methylthiophenyl-morpholinoketone), 4-Methylbenzophenone, 2-Methylbenzophenone, 1-Hydroxy cyclohexyl phenyl ketone, 2-Benzyl-2-(dimethylamino)-1-[4-(4-morpholinyl)phenyl]-1-butanone, Diphenyl Iodonium Hexafluorophosphate, Bis (p-tolyl)iodonium hexafluorophosphate, 2-Methyl-1-[4-(methylthio)phenyl]-2-morpholinopropanone-1, 2-Hydroxy-2-methyl-phenyl-propan-1-one, 1,7-bis(9-acridinyl)heptane, 2-Hydroxy-4'-hydroxyethoxy-2-methylpropiophenone, 2,2'-Bis(O-chlorophenyl-4,4',5,'-tetraphenyl-1,2'-diimidazole, 9-Phenylacridine, N-phenylglycine, 2-(4-methoxyphenyl-4,6-bis(trichloromethyl)-1,3,5-triazine, P-toluene sulfonylamine, Tris-(4-dimethylaminophenyl)methane, Tribromo methyl phenyl sulfone, 2,4-Bis(trichloromethyl)-6-(p-methoxy)styryl-s-triazine, 2,4-Bis(trichloromethyl)-6-(3,4-dimethoxy)styryl-s-triazine, 4-(2-aminoethoxy)methyl benzophenone, 4-(2-hydroxyethoxy)methyl benzophenone, 2-Isopropylthioxanthone, 4-Isopropylthioxanthone, 4-Hydroxy benzophenone, 4-Methyl acetophenone, 4-(4-Methylphenylthiophenyl)-phenylmethanone, dimethoxyphenylacetophenone, camphorquinone, 1-Chloro-4-propoxythioxanthone, 2-Chlorothioxanthone, 2,2-Diethoxyacetophenone, 2,4-Diethylthioxanthone, 2-Dimethyl-aminoethylbenzoate, 2-Ethylhexyl-4-dimethylaminobenzoate, Ethyl-4-(dimethylamino) benzoate, 2-Isopropylthioxanthone, Methyl o-benzoyl benzoate, Methyl phenyl glyoxylate, 4,4'-Bis(diethylamino) benzophenone, 4-Phenylbenzophenone, 2,4,6- and Ethyl (2,4,6-trimethylbenzoyl) phenylphosphinate. In some embodiments, the initiator is not camphorquinone. In some embodiments, the initiator is not ethyl O-dimethylaminobenzoate. In some embodiments, the initiator is not 4-N,N'-dimethylaminobenzoate.

The polymerization photoinitiators are used in amounts effective to initiate polymerization in the presence of the curing radiation, typically about 0.01 to about 10 wt %, about 0.05 to about 7 wt %, about 0.1 to about 5 wt %, about 0.5 to 2 wt %, or about 1.2 to 1.9 wt % based on the total weight of the composition.

The photoinitiator composition can optionally further contain a coinitiator for example, EHA (2-ethyl hexylacrylate) or an amine coinitiator such as, for example, ethyl-4-(dimethylamino)benzoate, 2-ethylhexyl dimethylaminobenzoate, dimethylaminoethyl (meth)acrylate, or the like. Reactive amine polymerization coinitiators can be used, such as the coinitiator CN386 (a reactive amine adduct of tripropylene glycol diacrylate), commercially available from Sartomer, Darocure EHA, or commercially available from Ciba, and the like. The coinitiator can be present in the composition in an amount of about 0.25 to about 20 wt %, specifically about 1 to about 10 wt %, and more specifically about 1 to about 5 wt %, based on the total weight of the composition. In a specific aspect the initiator is BAPO bis-acyl phosphine oxide commercially available, for example, as Irgacure from Ciba.

Chain Transfer Agents

In some embodiments, a chain transfer agent is employed. He chain transfer agent may be chosen from a range of thiol compounds including monofunctional and multifunctional thiols. Monofunctional thiols include, but are not limited to, propyl mercaptan, butyl mercaptan, hexyl mercaptan, octyl mercaptan, dodecyl mercaptan (docecanethiol, DDT), thioglycolic acid, methylbenzenethiol, dodecanethiol, mercaptopropionic acid, alkyl thioglycolates e.g. 2-ethyl hexyl thioglycolate or octylthioglycolate, mercaptoethanol, mercaptoundecanoic acid, thiolactic acid, thiobutyric acid. Multifunctional thiols include trifunctional compounds such as trimethylol propane tris(3-mercaptopropionate), tetrafunctional compounds such as pentaerythritol tetra(3-mercaptopropionate), pentaerythritol tetrathioglycolate, pentaerythritol tetrathiolactate, pentaerythritol tetrathiobutyrate; hexafunctional compounds such as dipentaerythritol hexa (3-mercaptopropionate), dipentaerythritol hexathioglycolate; octafunctional thiols such as tripentaerythritol octa(3-mercaptopropionate), tripentaerythritol octathioglycolate. The use of multifunctional thiols is a useful way to increase the degree of branching in the polymer. A difunctional chain transfer agent contains at least one thiol and at least one hydroxyl group. Examples of difunctional chain transfer agents include mercaptoethanol, mercaptopropanol, 3-mercapto-2-butanol, 2-mercapto-3-butanol, 3-mercapto-2-methyl-butan-1-ol, 3-mercapto-3-methyl-hexan-1-ol and 3-mercaptohexanol. Optionally, the chain transfer agent may comprise a mixture of more than one type of compound. In some embodiments, the chain transfer agent is docecanethiol. The amount of chain transfer agent present may be up to 50 wt % of the total initial monomer concentration. In a first embodiment, the amount of chain transfer agent present is 0.1-20% w/w, e.g. 0.5-10% w/w based on total monomer in the monomer mixture. The branched polymer is made using an appropriate amount of chain transfer agent to prevent the formation of a substantial amount of insoluble cross-linked polymer.

Surfactants

In some embodiments, the resin is modified by addition of a surfactant. In some embodiments, a surfactant is employed to increase the filler load in the polymerizable resin composition. In some embodiments, the filler surface is coated with a surfactant. The optional use of surfactant is hypothesized to increase the upper limit of the weight fraction of filler used in the filled compositions. In some embodiments, the surfactant is selected from anionic surfactants, based on sulfate, sulfonate or carboxylate anions, such as sodium dodecyl sulfate (SDS), ammonium lauryl sulfate, and other alkyl sulfate salts; cationic, based on quaternary ammonium cations such as Cetyl trimethylammonium bromide (CTAB), Cetylpyridinium chloride (CPC) and Polyethoxylated tallow amine (POEA); Zwitterionic surfactants, including amphoteric such as Dodecyl betaine and Dodecyl dimethylamine oxide, and nonionic surfactants, such as Alkyl poly(ethylene oxide), Copolymers of poly(ethylene oxide) and poly(propylene oxide) and Alkyl polyglucosides. In some embodiments, the surfactant is selected from sodium lauryl sulfate and polyether modified polydimethyl-siloxane (BYK®-307).

The hydrophilic-lipophilic balance (HLB) of a surfactant is an overall measure of the degree to which it is hydrophilic or lipophilic, and is determined by the ratio of polar and non-polar groups in the surfactant molecule. The HLB number of a surfactant indicates the polarity of the surfactant molecules in an arbitrary range of 1 to 40, wherein the number increases with increasing hydrophilicity. The HLB number for a surfactant can be determined by the "emulsion comparison method" of Griffin (W. C. Griffin, J. Soc. Cosmet. Chem. 1949, 1, 311-326). Alternatively, the HLB number can be estimated numerically or predicted by a variety of experimental techniques; see Guo et al., Journal of Colloid and Interface Science 2006, 298, 441-450; Ben-Et and Tatarsky, Journal of the American Oil Chemists' Society 1972, 49(8), 499-500; Trapani et al., International Journal of Pharmaceutics 1995, 116, 95-99; and the references cited therein.

Filled Compositions

In some embodiments, the disclosure provides a polymerizable composition comprising an acidic monomer, a urethane monomer and one or more hydrophobic monomers.

In some embodiments, the disclosure provides a polymerizable composition comprising a urethane monomer, an acidic monomer and two or more hydrophobic monomers.

In some embodiments, the disclosure provides a composition comprising an acidic monomer, a urethane monomer, two or more hydrophobic monomers, an initiator, and one or more fillers.

In some embodiments, the disclosure provides a composition comprising an acidic monomer, a urethane monomer, two or more hydrophobic monomers, an initiator, and two or more fillers with methacrylate silane surface treatment.

In some specific embodiments, the disclosure provides a preferred composition as follows:

Resin phase (referred to as the "standard resin")
Urethane dimethacrylate (UDMA) 51.2 wt %
Methacrylic acid (MAA) 18.8 wt %
Ethoxylated bisphenol A dimethacrylate (BisEMA) 22.5 wt %
Isostearyl methacrylate (ISMA) 7.5 wt %
Benzoyl peroxide (BPO) 1.8 wt %*

*Mass of BPO is based on the resin phase, so its weight fraction is not included in the other weight fraction designations Filler phase
Barium glass with methacrylate silane surface treatment (Ba glass)
Fumed silica with methacrylate silane surface treatment (OX50).

The dental materials of the present invention may optionally comprise additional adjuvants suitable for use in the oral environment, including colorants, flavorants, anti-microbials, fragrance, stabilizers, viscosity modifiers and fluoride releasing materials. For example, a fluoride releasing glass may be added to the materials of the invention to provide the benefit of long-term release of fluoride in use, for example in the oral cavity. Fluoroaluminosilicate glasses can be employed. Particularly preferred are silanol treated fluoroaluminosilicate glass fillers, as described in U.S. Pat. No. 5,332,429, the disclosure of which is expressly incorporated by reference herein. Other suitable adjuvants include agents that impart fluorescence and/or opalescence.

In some embodiments, the disclosure provides a method of using the dental material of the invention, comprising a hardenable resin, optional prepolymers, optional surfactants and fillers of the invention, the material is manipulated by the practitioner or laboratory to change the topography of the material, then followed by hardening the resin. These steps can be followed sequentially or in a different order. For example, in some embodiments where the dental material is a mill blank or prosthesis, the hardening step is generally completed prior to changing the topography of the material. Changing the topography of the material can be accomplished in various ways, such as carving or manual manipulation using hand held instruments, or by machine or computer aided apparatus, such as a CAD/CAM milling machine in the case of prostheses and mill blanks. Optionally, a finishing step can be performed to polish, finish, or apply a coating on the dental material.

The following examples are given to illustrate, but not limit, the scope of this invention. Unless otherwise indicated, all parts and percentages are by weight. Unless otherwise indicated, all numbers expressing quantities of ingredients, properties such as molecular weight, reaction conditions, and so forth used in the specification and claims are to be understood as being modified in all instances by the term "about." The term "about" represents +/−10% of the numerical term to which it is applied. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

EXAMPLES

Polymer flexural strength and modulus are calculated using a 3-point flexural test, carried out with a hydraulic universal test system (858 Mini Bionix, MTS Systems Corporation, Eden Prairie, Minn., USA) using a span width of 10 mm and a crosshead speed of 1 mm/min. The flexural strength (FS, σ) and flexural modulus (modulus, $E_f$) in MegaPascals (MPa) were calculated using the following equations:

$$\sigma = \frac{3Fl}{2bh^2} \quad \text{(Equation 2)}$$

$$E_f = \frac{F_1 l^3}{4bh^3 d} \quad \text{(Equation 3)}$$

where F is the peak load (in N), l is the span length (in mm), b is the specimen width (in mm), h is the specimen thickness (in mm); and d is the deflection (in mm) at load $F_1$ (in N) during the straight line portion of the trace (ISO/DIS 4049, 1987). ISO/DIS 4049 is the international standard for "Dentistry—Polymer-based filling, restorative and luting materials". Flexural strength test is one of the tests specified in this standard for the polymer-based filling, restorative and luting materials. In some embodiments, mechanical strength is tested on approximately eight specimens per sample (approximately 25 mm×2 mm×2 mm) and all samples are stored in water for 24 hours prior to flexural strength measurement.

Unless otherwise specified, photopolymerization is carried out using a VIP curing light (BISCO) at 500 mW/cm² for 40×3 seconds irradiation each side.

Near-Infrared spectroscopy (NIR) is performed on a Nicolet Nexus 670 to analyze degree of conversion during or following thermal polymerization.

Proton Nuclear Magnetic Resonance ($^1$H-NMR) can be used to integrate, thus quantify, protons of interest (Varian 300 MHz; performed in $CDCl_3$). For example, the $CH_2$ protons in EA, $CH_2OCH_2$ protons in TEGDMA, and $CH_3$ protons in dodecanethiol ($C_{12}SH$) at δ 1.92, 3.75-60, and 0.89 ppm chemical shifts, respectively, were integrated.

Gel permeation chromatography (GPC) using a Viscotek triple array detector system (refractive index, viscosity and light scattering detectors) is used to characterize the nanogels of the present invention in terms of $M_w$, polydispersity, and hydrodynamic radius. This data then verified that the composition did indeed form nanogels.

Atomic force microscopy (AFM) is used to study structural differences between nanogel particles. Topography of certain nanogels was evaluated with an AFM (SPI300; Seiko Instruments Inc., Chiba, Japan) using tapping mode with a spring constant of 15 N/m.

Example 1

Polymerizable Resin Compositions Comprising UDMA/MAA and EBDMA/ISMA

In the present example, unfilled photopolymers based on (UDMA/MAA)(EBDMA/ISMA) where the UDMA/MAA molar ratio is fixed at 1:2, which corresponds to a 73.2:26.8 weight ratio, and the EBDMA/ISMA weight ratio is fixed at 75:25. In Table 1, UDMA/MAA=A and EBDMA/ISMA=B.

TABLE 1

| Material A:B | Conversion, % | Modulus, GPa | Flexural strength, MPa |
|---|---|---|---|
| 100:0 | 93.6 | 3.11 ± 0.65 | 153.6 ± 44.7 |
| 80:20 | 94.0 | 4.61 ± 2.12 | 162.1 ± 25.3 |
| 75:25 | — | 3.05 ± 0.30 | 150.3 ± 50.3 |
| 70:30 | — | 3.08 ± 0.42 | 175.8 ± 47.9 |
| UDMA/EBDMA/ISMA | — | 2.66 ± 0.14 | 154.9 ± 14.4 |

From these results, the 80:20 material was selected to progress since it provided the best combination of both strength and stiffness along with high conversion. It is apparent that significant amounts of the nonhydrogen bonding comonomers can be included in the UDMA/MAA composition without sacrificing strength. However, when the MAA monomer was entirely omitted in a comonomer mixture, a decrease in the modulus was observed.

Composite materials were then prepared by mixing glass filler with selected resins. Various combinations of methacrylate silane-treated fillers were used that included particle diameters of 2 µm, 0.4 µm, 50 nm and 20 nm. Composite pastes with total filler contents of approximately 75 to 80 wt % were prepared using a centrifugal mixer. Mechanical strength results for some of the photopolymerized composite materials are given in Table 2.

TABLE 2

| Material | | Modulus, | Flexural | Vickers |
|---|---|---|---|---|
| resin | filler | GPa | strength, MPa | hardness # |
| UDMA/MAA/ EBDMA/ISMA | 0.4 µm/40 nm/20 nm (78 wt %) | 9.70 ± 0.95 | 88.0 ± 16.9 | 64.7 ± 9.7 |
| UDMA/EBDMA/ ISMA | 0.4 µm/ 20 nm (75 wt %) | 7.52 ± 0.30 | 127.7 ± 12.5 | 61.8 ± 8.7 |

The moduli values for the composites are significantly increased relative to the corresponding unfilled resin polymers as expected; however, the flexural strength results do not show the expected reinforcement effect and instead are reduced compared with their unfilled analogs. This is indicative of voids in the composite paste and polymer specimens that lead to localized stress concentration during mechanical testing. Improved mixing of the composite paste should alleviate this problem. In some embodiments, the filler loading level is increased to 85-90 wt % which should result in higher modulus, flexural strength and hardness values.

Example 2

Use of Surfactant

In another embodiment, the resin was modified by addition of a surfactant into the resin. Two surfactants were tested: 1 wt % sodium lauryl sulfate and BYK-307 (Polyether modified poly-dimethyl-siloxane). Two different resins were tested: a) UDMA/methacrylic acid/EBPADMA/ isostearyl methacrylate or b) UDMA/EBPADMA/isostearyl methacrylate. The incorporation of the surfactant allowed a standard 3-component filler weight fraction to be increased to just over 83 wt % of the total mass of the combined resin and filler.

The test results on these materials are as follows:

For resin a) with 1% sodium lauryl sulfate 11.9 (1.0) GPa flexural modulus; 132.4 (17.3) MPa flexural strength; 86.6 (2.8) Vickers hardness.

For resin a) with 1 wt % BYK-307 surfactant, 83.6 (1.8) Vickers hardness [values in ( ) are standard deviations].

For resin b) with 1 wt % sodium lauryl sulfate 10.2 (0.8) GPa flexural modulus; 128.4 (2.6) MPa flexural strength; 79.3 (2.2) Vickers hardness.

For resin b) with 1 wt % BYK-307 surfactant, 76.4 (3.1) Vickers hardness

In some embodiments, the composition includes one or more surfactants. In embodiments, the surfactants are selected from anionic (based on sulfate, sulfonate or carboxylate anions such as Sodium dodecyl sulfate (SDS), ammonium lauryl sulfate, and other alkyl sulfate salts), cationic (based on quaternary ammonium cations such as Cetyl trimethylammonium bromide (CTAB), Cetylpyridinium chloride (CPC) and Polyethoxylated tallow amine (POEA)), Zwitterionic (amphoteric such as Dodecyl betaine and Dodecyl dimethylamine oxide) and nonionic surfactants (such as Alkyl poly(ethylene oxide), In some embodiments, copolymers of poly(ethylene oxide) and poly(propylene oxide) and Alkyl polyglucosides) are suitable for this application.

In some embodiments, as in the above surfactant experiments, the surfactants are added to the resin. In some embodiments, the surfaces of the filler are coated with the surfactant prior to mixing the filler with the resin. In some embodiments, by coating the surface of the filler with surfactant, a reduced amount of surfactant is used while an increase in the upper limit of the weight fraction of filler is expected.

Example 3

Improved Flowability Resins

Further characterization work was performed related to improving the flowability of the resin. In an embodiment, the filler content is reduced to get into a range where there was enough flow to provide automated mold filling. In some embodiments, the filler content resulted in resin that exhibited little flow and was difficult to mold. Reducing the filler content reduced the hardness but, as shown below, the specifications of the resulting denture tooth are still well above the prior art; the strength was increased and the toughness also was good when compared to other teeth on the market.

In some embodiments, to improve flowability, it was determined that the comonomer composition and proportions need not be changed appreciably. In this embodiment, a quaternary comonomer mixture consisting of about 70 wt % of UDMA/MAA (in a molar ratio of 1:2) combined with about 30 wt % of EBPDMA/ISMA (in a 75:25 wt ratio) was investigated. The EBPDMA and ISMA content were raised to reduce the polymerization shrinkage and hydrophilicity, as it turns out without significantly compromising the strength and modulus of the polymer. In these experiments, Benzoyl peroxide was used as the thermal initiator (at 0.8-1.0 wt %), since nearly all commercial denture teeth are produced using thermal processing techniques.

Surface hardness (Vickers Hardness, VH)—Previous evaluation of hardness (examples 1-2) was conducted on moderate to highly filled materials:

1) 83 wt % filler (using a surfactant and a ternary filler that included ytterbium nanofiller along with barium glass and fumed silica), VH=86.6±2.8

2) 78 wt % filler (ternary filler without surfactant), VH=64.7±9.7

3) 55 wt % filler (binary filler of barium glass and fumed silica—both surface treated with a silane methacrylate), VH=40.1±0.1.

While the hardness in example 3 is reduced relative to the more highly loaded materials, this level of filler was selected to permit reasonable pressurized flow of the unpolymerized paste. This flow behavior is advantageous for a successful denture tooth material since the uncured paste should be able to flow into a tooth form mold. This level of filler provides a paste consistency that gives good flow and reliable reproduction of the mold form. The 78 or 83 wt % filler content produced such a heavy body material that it could not flow under reasonable pressures. However, with 55 wt % filler, the VH value of 40 is still significantly better than the VH values of ~20-24 exhibited by commercial acrylic and composite denture teeth. Even without the ytterbium filler as part of the formulation, the flexural strength of the low fill material in example 3 was 132.7±13.3 MPa, which is significantly stronger than the moderately filled analog (88.0±16.9 MPa; example 2) and equivalent to the strength of the highly filled material (132.4±17.3 MPa; example 1). Again, a key point is that example 3 is a material with a practical rheology, superior hardness to commercial denture teeth and excellent flexural strength.

Example 4

Toughness Compared to Commercial Composite Denture Tooth

In another study, the toughness of the material defined in example 3 was evaluated against a commercial composite denture tooth. Here, the toughness was defined as the integrated area under the stress-strain curve generated by the flexure strength testing in three-point bending. This comparison is valid since neither of these materials undergoes yielding prior to failure as is the case with acrylic (plastic) teeth. Our polymer toughness value was 180.4±46.3 for a material with a conversion of 90.7% and 231.5±60.2 for the same material at 86.2% conversion. In contrast, the commercial composite denture tooth had a toughness of only 96.5±18.6. If we measured toughness of a commercial plastic denture tooth up to the point that it undergoes yield deformation, then our material was also significantly tougher as well. In another comparison with commercial denture teeth, the flexural modulus of a commercial plastic or a composite tooth was 2.15±0.06 GPa or 2.45±0.15 GPa, respectively, while the modulus of the material described in example 3 was 6.24±0.25 GPa. This same material passed

Example 5

Compositions Comprising MMA and UDMA

To illustrate the difference in using MMA in place of MAA, a resin formulation was prepared with equimolar substitution of MMA in place of MAA. Unfilled resin bar-shaped specimens were prepared for conversion analysis and three-point bend mechanical testing. Using MAA, conversion was 96%, modulus was 3.5 GPA, and flexural strength was ~140 MPa. With MMA substituted for MAA, the same curing conditions yielded a conversion of <68%, a flexural modulus of 1.1 GPA, and a flexural strength of only 42 MPa. Therefore, the MAA is considered critical for the performance and high strength of the denture tooth material.

The strong hydrogen bonding reinforcement between the UDMA and MAA combined with the hydrophobic comonomers makes this resin system compositionally unique as well as novel in terms of the performance properties.

Surface hardness measurements as determined by Vickers indentation were as follows:

| Filled polymer | |
|---|---|
| 85 wt % filler (Ba glass/OX50) | 80.5 ± 2.8 |
| 75 wt % filler (Ba glass/OX50/Yb) | 64.7 ± 9.7 |
| 55 wt % filler (Ba glass/OX50/Yb) | 40.1 ± 0.1 |

For comparison, Vickers hardness of commercial denture tooth materials:

| | |
|---|---|
| SR Phonares NHC[a] | 30.2 ± 1.5 |
| Trublend SLM[b] | 27.9 ± 2.4 |
| Orthotyp PE[a] | 20.0 ± 0.2 |
| Orthosit PE[a] | 20.5 ± 0.1 |

[a]Ivoclar Vivadent;
[b]Dentsply Intl

Mechanical strength properties of externally processed denture tooth samples

| Composition* | Flexural modulus, GPa | Flexural strength, MPa |
|---|---|---|
| 60 wt % | 6.7 ± 0.5 | 134.3 ± 16.8 |
| 70 wt % | 9.8 ± 0.3 | 136.7 ± 33.3 |
| 85 wt % | 10.7 ± 0.6 | 186.5 ± 22.1 |

*Standard resin formulation with weight fraction of filler (9:1 mass ratio of Ba glass: OX50)

Properties for unfilled and filled materials prepared and processed internally

| | Unfilled resin | |
|---|---|---|
| Conversion, % | Flexural modulus, GPa | Flexural strength, MPa |
| Resin only | | |
| 96.5 ± 0.3 | 3.3 ± 0.2 | 198.2 ± 24.6 |
| Resin with prepolymer | | |
| 96.9 ± 0.4 | 2.6 ± 0.2 | 142.5 ± 15.3 |

| | Filled resin | |
|---|---|---|
| Conversion, % | Flexural modulus, GPa | Flexural strength, MPa |
| Resin only | | |
| 94.5 ± 0.1 | 8.1 ± 1.0 | 193.4 ± 11.5 |
| Resin with prepolymer | | |
| 94.3 ± 0.6 | 6.3 ± 0.3 | 141.5 ± 15.9 |

Curing protocol: Oven at 80° C. for 1 h, 110° C. overnight
Three point bending test: 10 mm span, 1 mm/min
Note: The resin containing the prepolymer used 2 wt % BPO; 1 wt % BPO used otherwise.

Example 6

Prepolymer

In some embodiments, a prepolymer can be used to reduce the overall volumetric shrinkage and improve the toughness of the polymer. The prepolymer can also be used to adjust the optical properties of the final composite denture tooth material by alteration of the refractive index of the resin phase through judicious selection of the monomers and their ratios used in the prepolymer synthesis. The prepolymer molecular weight should be great enough to achieve entanglement-based reinforcement (>10 kDa) but not overly high (>250 kDa) that leads to unnecessary viscosity rise in the monomeric state. The addition of the reactive sites within the prepolymer structure enhances the integration with the resin matrix upon polymerization and avoids the potential of polymerization-induced phase separation. The prepolymer-modified resin samples were completely transparent following polymerization at room temperature or at elevated curing temperatures, which indicates that the prepolymer was homogeneously dispersed in the resin and distributed in the final polymer network.

The use of MMA as the main component of the prepolymer was developed to facilitate interaction and bonding with a PMMA denture base materials. It is apparent that this prepolymer reduces the strength and the modulus of the final polymerized resin or composite polymers. We have also developed linear prepolymer with isobornyl methacrylate (IBMA) as the primary ingredient. The IBMA-based prepolymer has a glass transition temperature of >140° C., so this or other high Tg prepolymers, particularly those that present reactive functional groups for covalent integration with the resin matrix, are expected to produce final polymeric resin and composite materials that do not compromise mechanical property integrity as observed with the PMMA-type prepolymer. The prepolymer used in the prior results was prepared and formulated in the following manner:

Step 1: Prepolymer Preparation

| | |
|---|---|
| MMA (90 mol %) | 45 g |
| HEMA (10 mol %) | 6.5 g |
| AIBN (0.5 wt %) | 0.27568 g |
| Toluene | 120 mL |
| Dodecanethiol (7 mol % for Mn ~50 kDa) | 3.636 g |

Procedure:
1. Pre-heat oil bath to 65° C.
2. Add all reagents to round bottom flask, take IR spectrum (follow methacrylate conversion)

3. Attach condenser, let react for 6 h at 65° C., take IR spectrum (may need additional time at 80° C., until conversion reaches ≥90%)
4. Cool down, purify by precipitation in hexanes
5. Re-dissolve in acetone, remove solvent under reduced pressure, calculate yield
6. Characterize by NMR and GPC Step 2:

| | |
|---|---|
| Pre-polymer | 50 g |
| IEM (10% excess in relation to OH – NMR) | calculate |
| Methylene chloride | 200 mL |
| Dibutyl tin dilaurate | 2 drops |

Procedure:
1. Calculate OH content from NMR and amount of IEM needed to add an excess of 10 mol %
2. Dissolve the pre-polymer in methylene chloride, add IEM, take IR spectrum (follow isocyanate peak at 2270 cm$^{-1}$)
3. Add catalyst, allow to react for ~3 h at room temperature, take IR spectrum
4. Purify by precipitation in hexanes
5. Re-dissolve in acetone, remove solvent under reduced pressure (use 1 L round bottom flask; record the weight of the flask beforehand to calculate yield)
6. Characterize by NMR and GPC Step 3: Formulation of Prepolymer-Modified Resin

| | |
|---|---|
| Pre-polymer (dry; 20 wt % of resin) | 53.81 g |
| BisEMA (22.44 wt %) | 60.267 g |
| UDMA (51.28 wt %) | 137.969 g |
| ISMA (7.5 wt %) | 20.179 g |
| Acetone | 250 mL |
| Benzoyl peroxide (2 wt %) | 5.381 g |
| MEHQ (0.02 wt %) | 0.05381 g |
| Methacrylic acid (18.76 wt %) | 50.474 g |

Procedure:
1. Dissolve pre-polymer in acetone in a 1 L round bottom flask (to make it easier, use the same flask used to remove the solvent from the pre-polymer on the previous step; can only do this if weight of pre-polymer is known)
2. Add all other chemicals, except for methacrylic acid, and stir until homogeneous (use strong magnetic bar)
3. Remove acetone under reduced pressure, then add methacrylic acid and stir until homogeneous
4. Keep flask sealed in the refrigerator Filler can then be added between about 40 and 85 wt % with respect to the overall composite composition. The filler can be Ba glass, fumed silica, ytterbium fluoride (or other).

The filled or unfilled resin can be polymerized to high conversion (94-99% conversion) at temperatures as low as 80° C. The thermal curing process can be greatly accelerated by the introduction of a photoinitiator along with the BPO (or other appropriate thermal initiator) and the combination of photo/thermal processing. There are essentially no issues with volatility or porosity that result from the more compressed 2-3 minute photo/thermal curing protocol that lets even lower curing temperatures to be used with the much-shortened curing cycle. It should be noted that for denture teeth prepared with methyl methacrylate or other volatile monomers, the curing process is typically staged in an extended fashion that seeks to avoid a significant exotherm that could induce volatility issues.

The MAA monomer here has the greatest volatility potential of the components used; however MAA has a much lower vapor pressure and a much higher boiling point compared with MMA. To demonstrate this, a pre-weighed quantity of the standard resin composition filled with 55 wt % Ba glass/OX50 was manually spatulated open to the air for 5 minutes. The mass loss over the course of this active manipulation at room temperature was only 0.04 w %, which represents a negligible change in overall composition.

REFERENCES

1. Tanaka J, Hashimoto T, Stansbury J W, Antonucci J M, Suzuki K. Polymer properties of resins composed of UDMA and methacrylates with the carboxyl group. Dental Materials Journal 2001; 20:206-215.

We claim:

1. A polymerizable resin composition comprising a urethane monomer, wherein the urethane monomer is urethane dimethacrylate (UDMA), an acidic monomer, wherein the acidic monomer is methacrylic acid (MAA), and one or more hydrophobic monomers, and wherein the molar ratio of urethane monomer UDMA to acidic monomer MAA is about 1:2+/−20%.

2. The resin composition of claim 1, wherein the weight ratio of urethane monomers plus acidic monomers compared to hydrophobic monomers is selected from about 99:1 to 50:50.

3. The resin composition of claim 1 further comprising a surfactant.

4. The resin composition of claim 1 further comprising an initiator.

5. The resin composition of claim 1 further comprising a prepolymer.

6. The resin composition of claim 1, wherein the one or more hydrophobic monomers are selected from the group consisting of isostearyl methacrylate (ISMA), branched ISMA, ethoxylated bisphenol A dimethacrylate (EBDMA), stearyl methacrylate, lauryl methacrylate, isodecyl methacrylate, 2-ethylhexyl methacrylate and cyclohexyl methacrylate.

7. The resin composition of claim 3, wherein the surfactant is selected from sodium dodecyl sulfate (SDS), ammonium lauryl sulfate, Cetyl trimethylammonium bromide (CTAB), Cetylpyridinium chloride (CPC), Polyethoxylated tallow amine (POEA); Dodecyl betaine, Dodecyl dimethylamine oxide, sodium lauryl sulfate and polyether modified polydimethyl-siloxane.

8. The resin composition of claim 4, wherein the initiator is selected from a thermal initiator or a photoinitiator.

9. The resin of claim 8, wherein the thermal initiator is selected from the group consisting of 2,2'azobis(isobutyronitrile) (AIBN), azobis(2-methylbutyronitrile), azobis(2,4-dimethylvaleronitrile), 4,4-azobis(4-cyanovaleric acid), 1,1'-azobis(cyclohexanecarbonitrile); and a peroxide.

10. The resin composition of claim 5, wherein the prepolymer is formed from a resin composition comprising methyl methacrylate (MMA) or isobornyl methacrylate (IBMA).

11. A polymerizable dental restorative material comprising: particles of filler and the resin composition of claim 1.

12. The dental restorative material of claim 11, wherein the filler is present at 40 wt % to 90 wt % of the total material weight.

13. The dental restorative material of claim 11, wherein the filler is present at 70 wt % to 85 wt % of the total material weight.

14. The dental restorative material of claim 11, wherein the filler is present at 75 wt % to 80 wt % of the total material weight.

15. The resin of claim 9, wherein the peroxide is selected from the group consisting dilauroyl peroxide, tert-butyl peroxyneodecanoate, dibenzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-Butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butylperoxy isopropyl carbonate, cyclohexanone peroxide, dicumyl peroxide, lauroyl peroxide, 2,4-pentanedione peroxide, peracetic acid, cumyl peroxide, tert-butyl peroxy-2-ethyl hexanoate, tert-butyl peroxy diethyl acetate, tert-amyl peroxybenzoate, tert-butyl peroxy benzoate and benzoyl peroxide (BPO).

16. The resin composition of claim 2, wherein the weight ratio of urethane monomers plus acidic monomers compared to hydrophobic monomers is from about 90:10 to about 60:40.

17. The resin composition of claim 16, wherein the weight ratio of urethane monomers plus acidic monomers compared to hydrophobic monomers is from about 85:15 to about 75:25.

18. The resin composition of claim 16, wherein the weight ratio of urethane monomers plus acidic monomers compared to hydrophobic monomers is about 70:30.

19. The resin composition of claim 1, wherein the molar ratio of urethane monomer UDMA to acidic monomer MAA is about 1:2.

20. The resin composition of claim 6, wherein the hydrophobic monomer is selected from the group consisting of ethoxylated bisphenol A dimethacrylate (EBDMA) and branched isostearyl methacrylate (ISMA).

21. The resin composition of claim 20, wherein the hydrophobic monomer comprises ethoxylated bisphenol A dimethacrylate (EBDMA) and branched isostearyl methacrylate (ISMA) in about a 75:25 weight ratio.

22. A polymerizable resin composite composition comprising a resin phase and a filler phase, wherein the resin phase comprises:
  about 51.2 wt % Urethane dimethacrylate;
  about 18.8 wt % Methacrylic acid;
  about 22.5 wt % Ethoxylated bisphenol A dimethacrylate;
  about 7.5 wt % branched Isostearyl methacrylate, compared to total weight of combined urethane monomers, acidic monomers and one or more hydrophobic monomers in the resin phase of the polymerizable resin composition.

23. The polymerizable resin composite composition of claim 22, wherein the resin phase further comprises Benzoyl peroxide (BPO).

24. The polymerizable resin composite composition of claim 22, wherein the filler phase comprises a filler selected from the group consisting of barium glass, fumed silica, and ytterbium fluoride.

25. The polymerizable resin composite composition of claim 24, wherein the filler phase comprises from about 40 and 85 wt % with respect to the weight of the overall composite composition.

26. The polymerizable resin composite composition of claim 25, wherein the filler phase comprises a barium glass with methacrylate silane surface treatment (Ba glass) and/or a fumed silica with methacrylate silane surface treatment (OX50).

27. The polymerizable resin composite composition of claim 22, further comprising one or more additional adjuvants selected from the group consisting of colorants, flavorants, anti-microbials, fragrance, stabilizers, viscosity modifiers and fluoride releasing materials.

28. The polymerizable resin composition of claim 22, wherein after polymerization, the cured composite composition exhibits:
  i. surface hardness of at least 40 kgf/mm$^2$ as determined by Vickers indentation;
  ii. conversion of at least 92% when tested by near-infrared spectroscopy;
  iii. flexural modulus of at least 4 GPa when tested according to ISO/DIS 4049;
  iv. flexural strength of at least 88 MPa when tested according to ISO/DIS 4049.

29. The polymerizable resin composition of claim 28, wherein after polymerization, the cured composite composition exhibits flexural strength of at least 134 MPa when tested according to ISO/DIS 4049.

* * * * *